United States Patent
Ried et al.

(10) Patent No.: US 9,594,015 B2
(45) Date of Patent: Mar. 14, 2017

(54) METHOD AND DEVICE FOR DETERMINING RADICAL ATTRITION POTENTIAL

(71) Applicant: Xylem Water Solutions Herford GmbH, Herford (DE)

(72) Inventors: Achim Ried, Bad Oeynhausen (DE); Jens Scheideler, Schloss-Holte (DE); Arne Wieland, Minden (DE)

(73) Assignee: Xylem Water Solutions Herford GmbH, Herford (DE)

(*) Notice: Subject to any disclaimer, the term of this patent is extended or adjusted under 35 U.S.C. 154(b) by 1 day.

(21) Appl. No.: 14/403,757

(22) PCT Filed: Mar. 15, 2013

(86) PCT No.: PCT/EP2013/000799
§ 371 (c)(1),
(2) Date: Nov. 25, 2014

(87) PCT Pub. No.: WO2013/178304
PCT Pub. Date: Dec. 5, 2013

(65) Prior Publication Data
US 2015/0177127 A1 Jun. 25, 2015

(30) Foreign Application Priority Data
May 30, 2012 (DE) .................. 10 2012 010 611

(51) Int. Cl.
*G01N 21/33* (2006.01)
*G01N 21/31* (2006.01)
(Continued)

(52) U.S. Cl.
CPC ......... *G01N 21/33* (2013.01); *G01N 21/3151* (2013.01); *G01N 33/1893* (2013.01); *C02F 1/325* (2013.01); *C02F 1/722* (2013.01)

(58) Field of Classification Search
CPC .... G01N 21/33; G01N 33/18; G01N 33/1826; G01N 21/3151; C02F 1/00; C02F 1/32; C02F 1/325; C02F 1/722; C02F 1/72
See application file for complete search history.

(56) References Cited

U.S. PATENT DOCUMENTS

| 2004/0013777 A1* | 1/2004 | Hallstadius ............. A61L 2/208 426/320 |
| 2004/0045886 A1* | 3/2004 | Abe ........................ C02F 1/325 210/198.1 |

(Continued)

FOREIGN PATENT DOCUMENTS

| CN | 1372141 | 10/2002 |
| CN | 1869684 | 11/2006 |

(Continued)

OTHER PUBLICATIONS

Zachary F. Monge, Advanced Oxidation of Drinking Water using Ultraviolet Light and Alternative Solid Forms of Hydrogen Peroxide, Feb. 1, 2011, Envviornemtal & Water Resources Engineering, pp. 1-161.*

(Continued)

*Primary Examiner* — Michael P Lapage
(74) *Attorney, Agent, or Firm* — RatnerPrestia

(57) ABSTRACT

A method for the determination of the radical scavenging potential of a water, and includes determining the degradation of at least one reference substance in the water as a result of irradiation with UV light of at least one wavelength in the range of 100 to 350 nm, and a device for carrying out such determination with the aim of controlling a process for the oxidative treatment of water.

20 Claims, 2 Drawing Sheets

(51) Int. Cl.
*G01N 33/18* (2006.01)
*C02F 1/32* (2006.01)
*C02F 1/72* (2006.01)

(56) References Cited

U.S. PATENT DOCUMENTS

| | | | |
|---|---|---|---|
| 2004/0214335 A1* | 10/2004 | Li | A61L 2/0011 436/57 |
| 2005/0218082 A1 | 10/2005 | Williamson | |
| 2006/0240558 A1 | 10/2006 | Zhao | |
| 2008/0179178 A1 | 7/2008 | Cabello | |
| 2009/0101583 A1* | 4/2009 | Perry | B01D 61/58 210/664 |
| 2010/0206787 A1 | 8/2010 | Rozenberg | |

FOREIGN PATENT DOCUMENTS

| | | | | |
|---|---|---|---|---|
| DE | 4316452 | | 10/1994 | |
| EP | 0388590 | | 9/1990 | |
| EP | 1008556 | | 6/2000 | |
| GB | 2054843 | * | 2/1981 | ............ G01N 21/59 |
| JP | 09292388 | | 11/1997 | |
| WO | 2008049484 | | 5/2008 | |

OTHER PUBLICATIONS

International Preliminary Report on Patentability, dated Dec. 2, 2014, corresponding to counterpart International Application No. PCT/EP2013/000799, filed Mar. 15, 2013.
Rosenfeldt, E. J., Ph.D., PE et al., UV Advanced Oxidation Treatment of Emerging Contaminants In Drinking and Reuse Water, Sep. 2011, www.tawwa.org.
International Search Report, dated Jun. 7, 2013, corresponding to counterpart International Application No. PCT/EP2013/000799, filed Mar. 15, 2013.
International Search Report for International Application No. PCT/EP2013/000799 mailed Jun. 7, 2013.

\* cited by examiner

METHOD AND DEVICE FOR DETERMINING RADICAL ATTRITION POTENTIAL

CROSS-REFERENCE TO RELATED APPLICATIONS

This patent application is a U.S. National Phase Patent Application of PCT Application No. PCT/EP2013/000799, filed Mar. 15, 2013, which claims priority to German Patent Application No. 102012010611.4, filed May 30, 2012, each of which is incorporated by reference herein in its entirety.

FIELD OF THE INVENTION

The present invention relates to a method for the determination of the radical scavenging potential of a water, and comprises the determination of the degradation of at least one reference substance in the water as a result of irradiation with UV light of at least one wavelength in the range of 100 to 350 nm, and to a device for carrying out such a determination.

BACKGROUND OF THE INVENTION

To control AOP systems (AOP=Advanced Oxidation Process) for oxidative treatment, i.e. the oxidative preparation, purification and/or disinfection of water, parameters are currently used which give information about the composition of the water matrix and therefore determine scavenging of the generated radicals only indirectly. At present only the "conventional" parameters such as TOC, turbidity, UV-T and the measurement of specific parameters such as dissolved ozone or hydrogen peroxide are used to control AOP systems. These parameters are time-consuming to measure and the equipment to do so is usually expensive. Linking these parameters for control purposes is complex and depends on many different factors. Furthermore, the correlation between dose and effect (e.g. degradation of trace substances) is not known or can only be measured in a manner that is time-consuming since substance-specific analyses have to be carried out.

The scavenging (consumption) of OH radicals by the water matrix and measurement of this scavenging is so far unknown. At present too many OH radicals are produced in some installations (and consequently there is higher consumption of operating materials) in order to prevent the effect of "radical scavenging" ("scavenging"). Radical scavenging is caused by organic and inorganic substances that may be naturally present in water, such as carbonates for example.

CN 1869684 A, which is incorporated by reference herein, relates to a device and a method for measuring the oxygen demand of aerobic microorganisms during waste water treatment.

US 2006 240558 A, which is incorporated by reference herein, proposes a device and a method for determining the chemical oxygen demand (COD) of a water sample.

CN 1372141 A, which is incorporated by reference herein, discloses a test and evaluation method for the organic biobody degradation in water to attain extensive water quality targets using inter alia the parameters BOD5/COD, $CO_2$ formation and ATP.

JP 9292388 A, which is incorporated by reference herein, relates to a method for determining the degradation of a thin film of lubricant based on a fluorine-containing resin, with the concentration of fluoride ions being measured.

EP 0 388 590 A2, which is incorporated by reference herein relates to a method for determining organic compounds including all degradation products in a gas or liquid phase, with the gaseous or liquid sample material being transferred into a limited quantity of water in which the organic compounds are photolytically decomposed. The decomposition products are detected in a carrier gas and/or in the limited quantity of water.

DE 43 16 452 C1, which is incorporated by reference herein, describes a method for the degradation of polymeric organic pollutants in water by means of the AOP combination UV and hydrogen peroxide; there is no mention of a measuring method, however.

US 2010/0206787 A1, which is incorporated by reference herein, proposes a system for the treatment of liquids by means of UV radiation and an oxidising agent in an advanced oxidation process (AOP). The system is controlled by a regulating process, with the described measuring technique using two chemical sensors and determines the oxidizing agent content, in particular ozone, in the liquid phase and then controls the UV dose.

US 2008/0179178 A1, which is incorporated by reference herein, discloses a UV reactor for purifying waste water, likewise based on the AOP method. A UV light source and a titanium dioxide layer are used as catalyst to produce hydroxyl radicals, wherein this relates to the construction of the UV reactor required for this purpose for large-scale use and not to a measuring method for OH-radicals.

EP 1 008 556 A2, which is incorporated by reference herein, presents a method for the decontamination of polluted waste water by means of light radiation and ultrasound, i.e. a combined photo- and sonochemical treatment, it being possible for oxidizing agent such as ozone to also be used; there are no references to a measuring method, however.

A method for determining the radical scavenging potential of a water and its use for the efficient control of the consumption of operating materials in an AOP system has not been known until now.

It is therefore the object of the present invention to optimise or reduce the consumption of operating materials in ATP systems and methods and facilities for the oxidative treatment of water. In particular it is an aim of the present invention to disclose a method and a device for controlling a process for the oxidative treatment of water.

SUMMARY OF THE INVENTION

The present invention therefore provides
(i) a method for determining the radical scavenging potential of a water which contains the process-specific hydrogen peroxide concentration, comprising the determination of the degradation of at least one reference substance in the water as a result of irradiation with UV light;
(ii) a method according to (i), comprising the following steps
(1) adding at least one reference substance to a water sample and mixing all of said components,
(2) irradiation of the mixture obtained in step (1) with UV light of at least one wavelength in the range of 100 to 350 nm in an irradiation cell,
(3) measuring the absorption of the irradiated mixture obtained in step (2) with light of at least one wavelength in the range of 300-700 nm, preferably 600 to 660 nm,
(4) measuring the absorption of the untreated mixture obtained in step (1) as a comparison mixture at the same wavelength as in step (3) as a reference measurement, and (5) direct determination of the degradation of the reference substance as a degraded quantity of the reference substance from the difference between the measured values obtained in steps (3) and (4);

(iii) a method according to (i) or (ii), wherein the reference substance is a dye;

(iv) a method according to one of the embodiments (i) to (iii) for controlling the oxidative treatment of water, in particular the oxidative preparation, purification and/or disinfection of water;

(v) a device adapted to carry out a method as defined in embodiments (i) to (iv) and comprising
1) at least one reservoir containing a solution of at least one reference substance,
2) at least one mixing device for preparing a water sample by mixing the water with the at least one reference substance,
3) a two-way UV-irradiation device, in which in a chamber or cell (irradiation cell) the water sample issuing from the mixing device is irradiated with UV light and the intensity of the UV light is recorded preferably with a different chamber (comparison cell), wherein the two-way UV irradiation device has an emitted wavelength of 200 to 300 nm, and
4) a two-way photometer, in which in a chamber or cell (measuring cell) the absorption of the water sample issuing from the irradiation cell is measured with light of at least one wavelength in the range of 351 to 800 nm and in the other chamber (comparison measuring cell) the absorption of the untreated water sample (comparison sample) issuing from the mixing device is measured at the same wavelength as in the measuring cell; and (vi) a device according to embodiment (v) also comprising a controller for controlling the oxidative treatment of water.

BRIEF DESCRIPTION OF THE DRAWINGS

The method according to one embodiment of the invention and the technical components for this will be described with reference to the drawings comprising FIGS. 1 to 4.

DETAILED DESCRIPTION OF THE INVENTION

Figure 1:
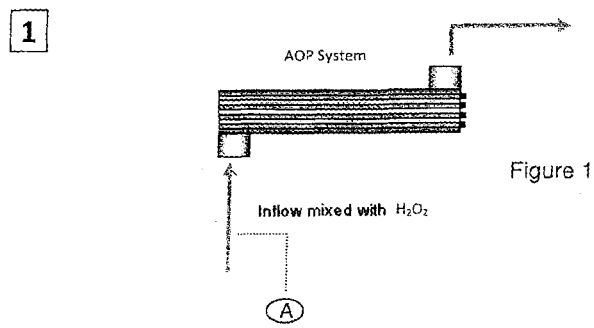
FIG. 1 shows the AOP system (AOP=Advanced Oxidation Process). The water is mixed with hydrogen peroxide and in this case passed to a UV irradiation phase (UV reactor). The UV irradiation can also be replaced by an ozone system. Part of the water is rerouted upstream of the intake of the treatment system into the online monitoring system and delivered to the assembly in FIG. 2.

The advantage of the invention described herein is the direct measurement of the radical scavenging behaviour of a water by way of the radical degradation of a reference substance, by way of example of methylene blue. The plant can be controlled more efficiently with regard to the operating costs by this parameter since the instantaneous scavenging of the OH radicals is determined directly and immediately and does not have to be estimated indirectly. Determination of this parameter and its combination with a second (standard) parameter (e.g. UV-T measuring) and the resulting control of an AOP system provides significant advantages which were not hitherto known since a final control concept has not existed until now.

The online monitoring system described here is based on the effect that a reference substance such as methylene blue can be degraded or decomposed by hydroxyl radicals. The degradation rate is affected by the organic and inorganic background of the water to which the reference substance has been added.

The reference substance is degraded in an irradiation chamber in which a defined UV light dose is used and the necessary hydroxyl radicals are formed. The UV dose is registered and controlled by using a comparison chamber which is filled with air.

The degradation rate of the reference substance can be determined with the aid of the measurement of visible light, in the case of the use of methylene blue as reference substance at a wavelength of 600 to 660 nm, a comparison sample (not irradiated with UV light) and the treated sample. The result of this measurement is the radical scavenging potential of the water matrix.

Since the performance of an oxidative treatment system, like advanced oxidation processes, is crucially affected by the organic or inorganic background (scavenging potential) of the water, an online monitoring system, which the described method uses, would be capable of adjusting and controlling the treatment system, and this leads to savings in terms of operating costs and ensures that all treatment targets are attained.

For the purpose of controlling the oxidative treatment of water, which is taken to mean in particular the oxidative preparation, purification, and/or disinfection of water, in particular by using different method steps such as UV radiation, hydrogen peroxide or ozone or a combination thereof, and a facility for said fields of use, the degradation rate ascertained with the method according to aspects of the invention is suitable as a control or measured value: the metering of the method steps involved in radical formation (radical formers) depends on the ascertained radical scavenging rate, i.e. primarily the irradiation of water with UV-radiation, the quantity of hydrogen peroxide added to the water and/or the quantity of ozone added to the water. The higher the ascertained scavenging rate is, the higher at least one radical former is metered, the lower the ascertained degradation rate is, the lower at least one radical former is metered. This type of control can ensure an optimum, optimally sparing use or consumption of the radical formers or operating materials.

Particularly effective in the oxidative treatment of water and therefore preferred according to aspects of the invention are combinations of the used radical formers, i.e. UV radiation and hydrogen peroxide, UV radiation and ozone, hydrogen peroxide and ozone and UV radiation, hydrogen peroxide and ozone respectively.

The UV light described in step (2) and used for the irradiation of the water has a wavelength of 100 to 350 nm, preferably of 150 to 300 nm, particularly preferably 254 nm. The irradiation of the water sample, which may contain for example hydrogen peroxide, with UV light is used to produce the hydroxyl radicals. This irradiation takes place in a defined period. A pre-selected period between 1 second and 1 hour may be provided by way of example.

In the method according to aspects of the invention the intensity of the UV light used in step (2) is determined by a simultaneous comparison measurement with a comparison cell which is filled with a gas, preferably with air, and registered.

The choice of wavelength of the light that is used for measurement of the absorption of the irradiated mixture obtained in step (3) depends on the reference substance used, in particular its absorption maxima, i.e. light of wavelength (s) at which the absorption maxima of the reference substance lie is preferably used. According to aspects of the invention light of at least one wavelength in the range of 300-700 nm, preferably 600 to 660 nm, can be used. The absorption is preferably measured photometrically.

The reference substance(s) is preferably a substance that absorbs in visible light in a wavelength range of 300 to 700 nm. Particularly preferred as reference substance is the dye methylene blue.

The colouring of the water, which is caused by the reference substance, is measured by the irradiation of the reference sample and the treated sample from step (2). Irradiation preferably occurs
(a) in step (3) over a pre-selectable or pre-selected period, for example between 1 second and 1 hour, and
(b) measuring takes place in step (4) at the same time as measuring in step (3), as described in (a).

Determination of the degradation of the reference substance includes in particular determination of the degradation rate of this reference substance. This degradation rate can be determined in particular by plotting over time at least two of the differential values obtained in step (5).

In the method according to aspects of the invention steps (1) to (5) preferably occur one after the other in accordance with the numbering, i.e. step (2) follows step (1), step (3) follows step (2), etc. Steps (3) and (4) preferably occur at the same time or substantially at the same time in order to thus be able to reproduce the intensities at the individual absorption wavelengths independently of the characteristics of the apparatus and the inherent absorption of the measuring cell.

The method according to aspects of the invention is suitable in particular for controlling systems for the oxidative treatment of water, in particular the oxidative preparation, purification and/or disinfection of water. The systems can comprise a combination of the following components, with the parameter to be controlled also being described here:
(a) irradiation with UV light in the range of 100 to 350 nm and control of this irradiation,
(b) the addition of hydrogen peroxide and control of the addition of hydrogen peroxide,
(c) the addition of ozone and control of the metering of ozone.

The water that contains the actual concentration of hydrogen peroxide is led via a bypass to the device. If the water should not contain any hydrogen peroxide as result of the process then the water must be supplied with it upstream of the device by way of a mixing unit.

The device for carrying out the method according to aspects of the invention includes
1) at least one reservoir containing a preferably aqueous solution of at least one reference substance used according to aspects of the invention,
2) at least one mixing device for preferably homogeneous mixing of the water described above with at least one reference substance (1),
3) a two-way UV-irradiation device, in which in a chamber or cell (irradiation cell) the water sample issuing from the mixing device defined in (2) is irradiated with UV light and the intensity of the UV light is recorded preferably with a different chamber (comparison cell), wherein the two-way UV irradiation device has a wavelength of 200 to 300 nm, and
4) a two-way photometer, in which in a chamber or cell (measuring cell) the absorption of the water sample issuing from the irradiation cell in (3) is measured with light of at least one wavelength in the range of 351 to 800 nm and in the other chamber (comparison measuring cell) the absorption of the untreated water sample (comparison sample) issuing from the mixing device defined in (2) is measured at the same wavelength as in the measuring cell.

If it is being used to control the oxidative treatment of water, in particular the oxidative preparation, purification, and/or disinfection of water, the device can also include a treatment system or AOP system for the oxidative treatment, in particular the oxidative preparation, purification, and/or disinfection of water, and control this treatment system.

FIG. 1 shows the AOP system (AOP=Advanced Oxidation Process). The water is mixed with hydrogen peroxide and in this case passed to a UV irradiation phase (UV reactor). The UV irradiation can also be replaced by an ozone system. Part of the water is rerouted upstream of the intake of the treatment system into the online monitoring system and delivered to the assembly in FIG. 2.

Figure 2:
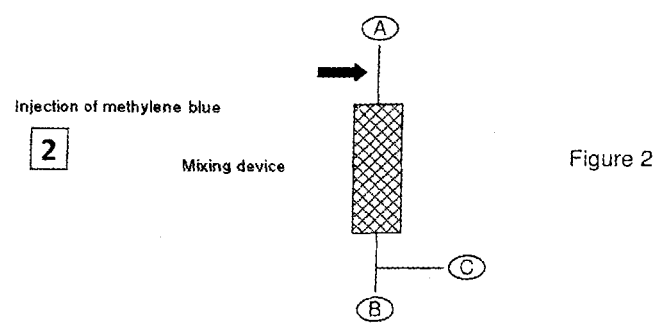
FIG. 2 shows the addition of methylene blue. A methylene blue stock solution is added to the water and mixed in such a way that all of the methylene blue is homogeneously distributed in the water sample. Part of this mixture passes to the irradiation phase with UV radiation in the assembly in FIG. 3. Another part of this mixture is transferred as a reference sample to FIG. 4.

FIG. 2 shows the addition of methylene blue. A methylene blue stock solution is added to the water and mixed in such a way that all of the methylene blue is homogeneously distributed in the water sample. Part of this mixture passes to the irradiation phase with UV radiation in the assembly in FIG. 3. Another part of this mixture is transferred as a reference sample to FIG. 4.

Figure 3:
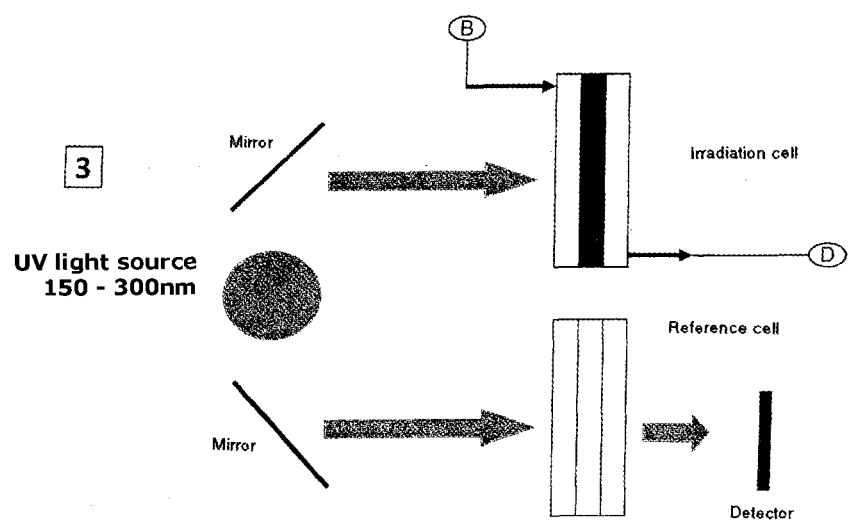
FIG. 3 shows a two-way UV irradiation device in which in a chamber or cell the water sample from FIG. 2 is irradiated with UV light and the intensity of the UV light is recorded in the other chamber (comparison cell). After irradiation the water sample is transferred to step 4 (FIG. 4).

FIG. 3 shows a two-way UV irradiation device in which in a chamber or cell the water sample from FIG. 2 is irradiated with UV light and the intensity of the UV light is recorded in the other chamber (comparison cell). After irradiation the water sample is transferred to step 4 (FIG. 4).

Figure 4:
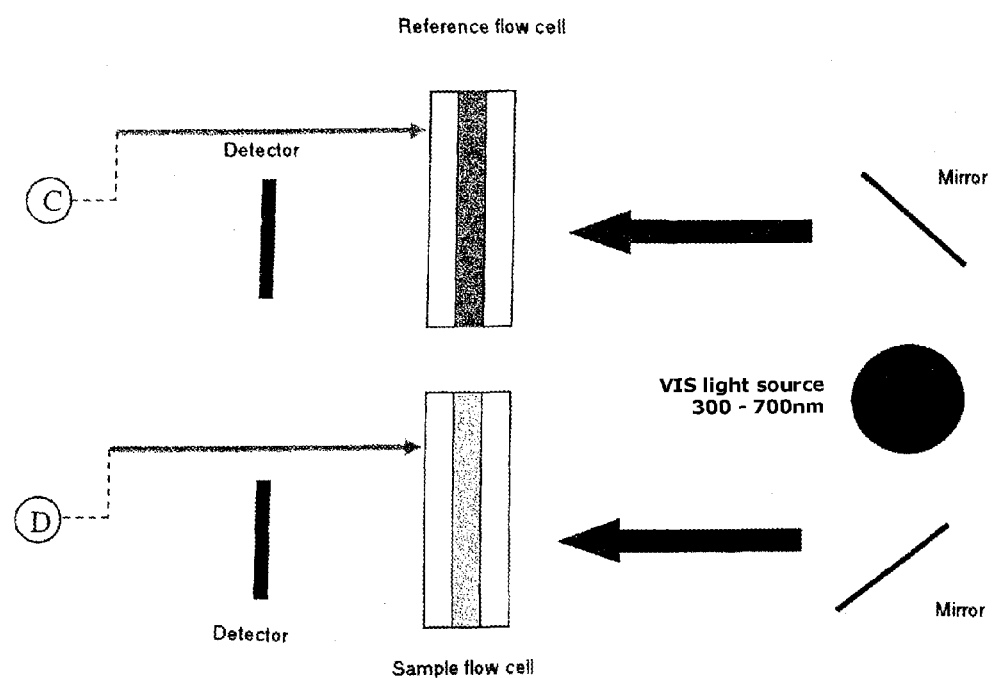
FIG. 4 shows a two-way photometer in which in a chamber or cell the absorption of the UV irradiated water sample from FIG. 3 is measured at wavelengths of 600 to 660 nm and in the other chamber the absorption of the untreated sample comprising methylene blue is mixed with water (comparison sample) from FIG. 2 is measured at the same wavelengths.

FIG. 4 shows a two-way photometer in which in a chamber or cell the absorption of the UV irradiated water sample from FIG. 3 is measured at wavelengths of 600 to 660 nm and in the other chamber the absorption of the untreated sample comprising methylene blue is mixed with water (comparison sample) from FIG. 2 is measured at the same wavelengths.

This method directly determines the degradation of the methylene blue by way of the difference in absorption. After measuring, the water sample can be discarded or returned to the water treatment system.

The invention claimed is:
1. A method for determining a radical scavenging potential of a water by determining a degradation of at least one reference substance in the water as a result of irradiation with ultraviolet (UV) light from a UV irradiation device, said method comprising the following steps:

(1) adding at least one reference substance to a water sample and then mixing the water sample, (2) irradiating a first portion of the mixture obtained in step (1) with UV light from the UV irradiation device of at least one first wavelength in the range of 100 to 350 nm in an irradiation cell, the first wavelength operative to at least partially degrade the least one reference substance, (3) measuring an absorption of a quantity of the irradiated mixture obtained in step (2) in a measurement cell using light of at least second one wavelength in a range of 300 nm to 700 nm, (4) measuring the absorption of a second portion of the mixture obtained in step (1), which portion has not been irradiated by the UV light from the UV irradiation device in step (2), in a comparison measurement cell using light of the same wavelength as in step (3) as a reference measurement, and (5) determining the degradation of the reference substance caused by step (2) from a difference between the measured values obtained in steps (3) and (4).

2. The method according to claim 1, wherein the radical scavenging potential relates to scavenging potential of radicals comprising hydroxyl radicals.

3. The method according to claim 1, wherein hydrogen peroxide is used to form the radicals.

4. The method according to claim 1, wherein the reference substance is a substance which absorbs light in a wavelength range from 300 to 700 nm.

5. The method according to claim 4, wherein determining the degradation of at least one reference substance includes determining a degradation rate of the reference substance which absorbs in light in a wavelength range from 300 to 700 nm.

6. The method according to claim 1 further comprising simultaneously recording an intensity of the UV light in step (2) by way of a comparison measurement with a comparison cell.

7. The method according to claim 1, wherein
(a) irradiation takes place in step (2) over a pre-selectable period of 1 second to 1 hour,
(b) measuring takes place in step (3) over a pre-selectable period of 1 second to 1 hour, and/or
(c) measuring takes place in step (4) at the same time as measuring in step (3).

8. The method according to claim 1, wherein a degradation rate of at least one reference substance is determined by plotting over time at least two differential values obtained in step (5).

9. The method according to claim 1, wherein the steps (1) to (5) are carried out one after the other from step (1) to step (5).

10. The method according to claim 1, wherein the determination of the radical scavenging potential of the water is used for controlling an oxidative treatment of water.

11. The method according to claim 10, wherein the oxidative treatment includes
(a) irradiation with UV light in the range of 100 to 350 nm, and/or
(b) adding hydrogen peroxide, and/or
(c) adding and metering ozone.

12. The method of claim 1, comprising performing the method using a device comprising:
1) at least one reservoir containing a solution of the at least one reference substance,
2) at least one mixing device for preparing the water sample by mixing the water with the at least one reference substance,
3) the UV irradiation device, in which in the irradiation cell the first portion of the water sample issuing from the mixing device is irradiated with UV light and an intensity of the UV light is recorded with a comparison cell, wherein the UV light has an emitted wavelength of 100 to 350 nm, and
4) a photometer, in which in the measurement cell the absorption of the first portion of the water sample issuing from the irradiation cell is measured and in the comparison measurement cell the absorption of the second portion of the water sample issuing from the mixing device but not irradiated by the UV irradiation device is measured at the same wavelength as in the measurement cell.

13. The method according to claim 12, further comprising providing the output of the device as an input to a controller to control oxidative treatment of water.

14. The method according to claim 1, wherein steps (3) and (4) are carried out at the same time or substantially at the same time.

15. The method according to claim 1 for controlling an oxidative preparation, purification, and/or disinfection of water.

16. The method according to claim 1, wherein the reference substance is methylene blue.

17. The method of claim 16, wherein the light used in steps (3) and (4) has at least one wavelength in the range of 600-660 nm.

18. The method of claim 1, wherein the UV light used in step (2) has at least one wavelength in the range of 200-300 nm.

19. The method of claim 18, wherein the UV light used in step (2) has a wavelength of 254 nm.

20. The method of claim 1, further comprising determining a rate of degradation of the reference substance by comparing two of the differences measured in step (5) over time.

* * * * *